US010219082B2

(12) United States Patent
Nielsen

(10) Patent No.: US 10,219,082 B2
(45) Date of Patent: Feb. 26, 2019

(54) METHOD OF OPERATING A HEARING AID SYSTEM AND A HEARING AID SYSTEM

(71) Applicant: Widex A/S, Lynge (DK)

(72) Inventor: Jakob Nielsen, Copenhagen (DK)

(73) Assignee: Widex A/S, Lynge (DK)

( * ) Notice: Subject to any disclaimer, the term of this patent is extended or adjusted under 35 U.S.C. 154(b) by 0 days.

(21) Appl. No.: 15/626,333

(22) Filed: Jun. 19, 2017

(65) Prior Publication Data
US 2017/0289708 A1 Oct. 5, 2017

Related U.S. Application Data

(63) Continuation-in-part of application No. PCT/EP2014/078760, filed on Dec. 19, 2014.

(51) Int. Cl.
H04R 25/00 (2006.01)
A61B 5/12 (2006.01)
A61B 5/00 (2006.01)

(52) U.S. Cl.
CPC ........... *H04R 25/505* (2013.01); *A61B 5/128* (2013.01); *A61B 5/725* (2013.01); *A61B 5/7242* (2013.01); *H04R 25/552* (2013.01); *H04R 25/554* (2013.01); *H04R 25/75* (2013.01); *H04R 2225/43* (2013.01)

(58) Field of Classification Search
CPC .................................................. H04R 25/505
USPC ...... 381/17, 23.1, 94.7, 315, 317, 318, 94.3, 381/312, 320; 600/28; 704/200.1
See application file for complete search history.

(56) References Cited

U.S. PATENT DOCUMENTS

| 4,628,529 | A | * | 12/1986 | Borth | G10L 21/0208 381/317 |
| 4,791,672 | A | * | 12/1988 | Nunley | H04R 25/505 381/317 |
| 4,887,299 | A | * | 12/1989 | Cummins | H04R 25/356 381/317 |
| 5,027,410 | A | * | 6/1991 | Williamson | H04R 25/453 381/314 |
| 6,097,824 | A | | 8/2000 | Lindermann et al. | |
| 7,292,699 | B2 | * | 11/2007 | Gao | H03H 21/0012 381/318 |
| 2002/0118851 | A1 | * | 8/2002 | Paludan-Mueller | H04R 25/356 381/317 |
| 2003/0072464 | A1 | * | 4/2003 | Kates | G10H 1/125 381/312 |
| 2010/0254555 | A1 | * | 10/2010 | Elmedyb | H04R 25/453 381/318 |
| 2011/0054241 | A1 | * | 3/2011 | Jensen | H04R 25/75 600/28 |
| 2012/0239385 | A1 | * | 9/2012 | Hersbach | G10L 25/84 704/200.1 |

(Continued)

FOREIGN PATENT DOCUMENTS

| EP | 10 2011 001 793 A1 | 10/2012 |
| WO | 2011/043678 A1 | 4/2011 |
| WO | 2014/094867 A1 | 6/2014 |

OTHER PUBLICATIONS

International Search Report for PCT/EP2014/078760 dated Sep. 2, 2015 [PCT/ISA/210].

*Primary Examiner* — Gerald Gauthier
(74) *Attorney, Agent, or Firm* — Sughrue Mion, PLLC

(57) ABSTRACT

A hearing aid system (100, 200) adapted for providing an enriched sound and a method of providing such an enriched sound.

23 Claims, 2 Drawing Sheets

(56) References Cited

U.S. PATENT DOCUMENTS

| | | | |
|---|---|---|---|
| 2012/0263329 A1* | 10/2012 | Kjeldsen | H04R 25/505 381/315 |
| 2013/0051566 A1* | 2/2013 | Pontoppidan | H04R 25/353 381/23.1 |
| 2013/0208896 A1* | 8/2013 | Chatlani | H04R 25/407 381/17 |
| 2014/0177868 A1* | 6/2014 | Jensen | H04R 3/002 381/94.7 |
| 2017/0289708 A1* | 10/2017 | Nielsen | H04R 25/505 |

* cited by examiner

METHOD OF OPERATING A HEARING AID SYSTEM AND A HEARING AID SYSTEM

This application is a Continuation in part of International Application No. PCT/EP2014/078760, filed on Dec. 19, 2014, the contents of all of which are incorporated herein by reference in their entirety.

The present invention relates to a method of operating a hearing aid system. The invention more specifically relates to a method of generating enriched sound. The invention also relates to a hearing aid system.

BACKGROUND OF THE INVENTION

Generally a hearing aid system according to the invention is understood as meaning any device which provides an output signal that can be perceived as an acoustic signal by a user or contributes to providing such an output signal, and which has means which are customized to compensate for an individual hearing loss of the user or contribute to compensating for the hearing loss of the user. They are, in particular, hearing aids which can be worn on the body or by the ear, in particular on or in the ear, and can be fully or partially implanted. However, those devices whose main aim is not to compensate for a hearing loss but which have, however, measures for compensating for an individual hearing loss are also concomitantly included, for example consumer electronic devices (televisions, hi-fi systems, mobile phones, MP3 players etc.).

Within the present context a traditional hearing aid can be understood as a small, battery-powered, microelectronic device designed to be worn behind or in the human ear by a hearing-impaired user. Prior to use, the hearing aid is adjusted by a hearing aid fitter according to a prescription. The prescription is based on a hearing test, resulting in a so-called audiogram, of the performance of the hearing-impaired user's unaided hearing. The prescription is developed to reach a setting where the hearing aid will alleviate a hearing loss by amplifying sound at frequencies in those parts of the audible frequency range where the user suffers a hearing deficit. A hearing aid comprises one or more microphones, a battery, a microelectronic circuit comprising a signal processor, and an acoustic output transducer. The signal processor is preferably a digital signal processor. The hearing aid is enclosed in a casing suitable for fitting behind or in a human ear.

A traditional hearing aid system may comprise hearing aids for both the left and right ear and in that case be denoted a binaural hearing aid system. However as discussed above a hearing aid system needs not be binaural.

In the context of the present disclosure, an enriched sound should be understood as a sound having a quality whereby it is easy to relax and be relieved of e.g. stress and anxiety when subjected to it. The sounds of nature are one example of enriched sound.

It has been suggested within the art of tinnitus alleviation to use enriched sound as a means of disguising silence, whereby the brain's attention may be diverted away from the silence and hereby away from the tinnitus. Additionally, people suffering from tinnitus may benefit from enriched sound since this can lessen the perceived contrast between the tinnitus and the sound environment.

Tinnitus Retraining Therapy (TRT) is another method that has been used to try to alleviate tinnitus. TRT methods generally use white noise provided to the tinnitus patient at a level below the tinnitus.

EP-B1-2132957 discloses a sound enrichment system for the provision of tinnitus relief, wherein a noise signal is random or pseudo-random modulated whereby the monotony of the noise signal is reduced and the resulting sound made more comfortable to listen to for many users. Random modulation of the amplitude and the frequency characteristics of the noise signal are disclosed.

One problem with this system is that despite the fact that the monotony of the noise signal is reduced, many users may still find the sounds uncomfortable to listen to. This may especially be the case for the prolonged time of use required by most TRT methods.

U.S. Pat. No. 6,816,599 B2 discloses one type of enriched sound that can be generated by a music synthesizer in a way that is very well suited for implementation in e.g. a hearing aid.

It is a feature of the present invention to provide a method for the generation of enriched sound with improved listening comfort.

It is another feature of the present invention to provide a hearing aid and a hearing aid system adapted to provide enriched sound with improved listening comfort.

It is yet another feature of the present invention to provide enriched sound that has a broad frequency spectrum and is comfortable to listen to.

SUMMARY OF THE INVENTION

The invention, in a first aspect, provides a method of operating a hearing aid system according to claim 1.

This provides a method whereby enriched sound with improved listening comfort is achieved.

The invention, in a second aspect, provides a hearing aid system according to claim 18.

This provides an improved hearing aid system.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

In the present context the terms frequency band and frequency band signal may be used interchangeably. Furthermore the term signal level may in the following be used to mean the predicted sound output level. Hereby improving the ease of reading the disclosure e.g. when discussing the signal level relative to the hearing threshold.

Figure 1:
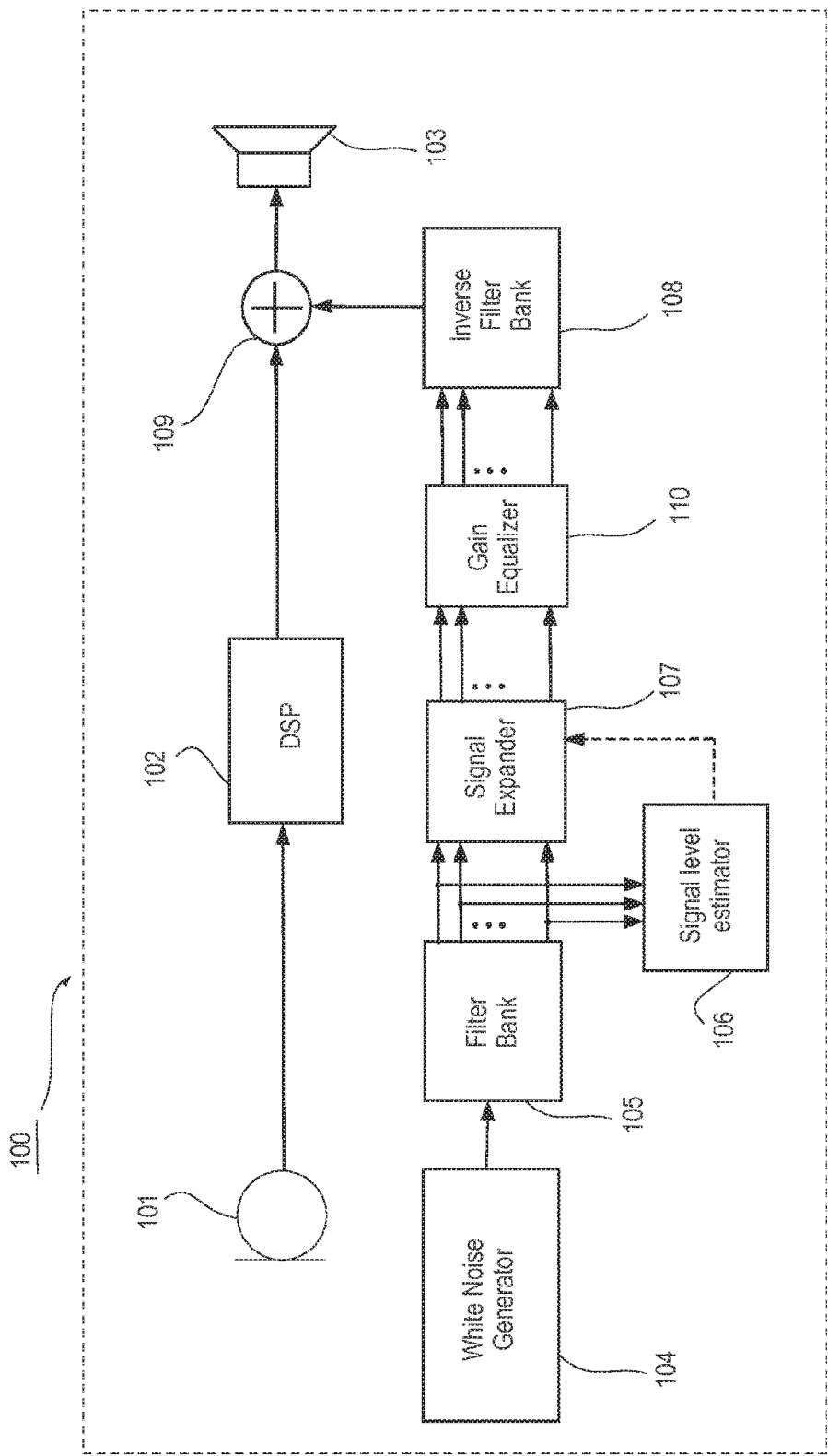
FIG. 1 illustrates highly schematically a hearing aid system according to a first embodiment of the invention.

Reference is first made to FIG. 1, which illustrates highly schematically a hearing aid system 100 according to an embodiment of the invention.

The hearing aid system 100 comprises an acoustical-electrical input transducer 101, a digital signal processor (DSP) 102 adapted to alleviate a hearing deficit, an electrical-acoustical output transducer 103, a white noise generator 104, a filter bank 105, a signal level estimator 106, a signal expander 107, a gain equalizer 110 an inverse filter bank 108 and a summing node 109.

The white noise generator 104 is a standard component that is well known within the art of hearing aids. According to the present embodiment a Maximum Length Sequence (MLS) generator is used that provides a sequence with a duration of only 16 seconds.

However, in variations basically any random generator can be used although the MLS generator is advantageous for use in hearing aid systems due to its simple implementation. In other variations longer sequences may be used in order to seek to improve the perceived quality of the provided sound. However, it is a specific advantage of the present invention that a sequence of such a short duration may be sufficient to provide a sound that is not perceived as monotonous to listen to, whereby the requirements to processing power and complexity of implementation may be relieved.

In still further variations colored noise, such as pink and brown noise may be used instead of white noise.

The white noise signal provided by the white noise generator 104 is split into 15 frequency band signals by filtering in the filter bank 105.

In variations the white noise signal is split into additional frequency bands or fewer frequency bands such as in the range between 5 and 50 frequency bands. Generally the inventor has found that the use of additional frequency bands provides a more slow modulation of the signal in each frequency band. Particularly the inventor has found that by using say 30 frequency bands a sound resembling bubbling water can be provided.

According to the present embodiment the frequency bands cover the frequency range from 0-15 kHz.

However, in less preferred variations it may be selected to cover a smaller range such as from 1 kHz to 10 kHz. Most people may perceive sound based on such a more narrow frequency range as less attractive to listen to, but these sounds will at least cover most of the frequency range where e.g. tinnitus is typically located.

It is noted as a specific advantage of the present embodiment that sounds that resemble naturally occurring sounds have relative large high frequency content, which is a desired property for e.g. people suffering from tinnitus. Most music, as opposed hereto, is characterized in that the amount of energy in the high frequency range may in some case not be sufficient to provide effective partial masking of a tinnitus in the high frequency range. One may consider shaping the music in order to provide more energy in the high frequency range but most people will perceive the resulting quality of the music as quite poor due to perceived shrillness of the sound.

The signal levels of the frequency band signals are branched and provided both to the signal level estimator 106 and to the signal expander 107.

The signal level estimator 106 estimates the signal level $y_k(n)$ for a given frequency band signal k and for a sample n in accordance with:

$$y_k(n)=|x_k(n)|\times\alpha_k+y_k(n-1)\times(1-\alpha_k)$$

wherein $y_k(n-1)$ is the previous signal level estimate of the given frequency band signal, $x_k(n)$ is the current value of the given frequency band signal and $\alpha_k$ is a constant that determines how close the signal level estimate follows the current value of the given frequency band signal. Thus $\alpha_k$ is a constant that determines the time constant of the signal level estimation.

The current value $x_k(n)$ of the given frequency band signal is sampled with a frequency of 32 kHz and correspondingly the signal level estimate $y_k(n)$ is updated with the same frequency. In variations of the present embodiment it may be selected to sample the lower frequency bands at a lower frequency such as 16 kHz whereby the use of processing resources may be relieved. In still further variations the a signal sampled at a relatively low frequency may subsequently be up-sampled to match the sampling frequency of the hearing aid system.

According to the present embodiment the value of $\alpha_k$ is selected to be smaller in the lower frequency bands than in the higher frequency bands and such that in the lowest frequency band a value of 0.003 is selected and in the highest frequency band a value of 0.042 is selected. Hereby the signal level estimate is allowed to follow relatively closely the current value of even the higher frequency bands. According to a specific embodiment the values of $\alpha_k$ listed from lowest to highest frequency band are selected to be: 0.003, 0.003, 0.003, 0.003, 0.003, 0.002, 0.003, 0.003, 0.003, 0.006, 0.007, 0.009 0.010, 0.022, 0.042.

In variations of the present embodiment the value of $\alpha_k$ may be selected to be the same in all the frequency bands. In yet further variations the value of $\alpha_k$ is selected from the range between 0.0 and 0.1 independent on whether the value is the same in all the frequency bands or increases with the center frequency of the frequency bands.

The signal expander 107 applies a gain to the current value $x_k(n)$ of the given frequency band signal, hereby providing a processed current value $z_k(n)$ of the given frequency band signal.

The gain $G_k'(n)$, given in dB, is calculated as:

$$G_k'(n)=(y_k'(n)-k_{ref}')k_{expand}$$

wherein $y_k'(n)$ represents the value of $y_k(n)$ in the dB domain, $k_{ref}'$ is a constant that represents the value of a reference level in the dB domain and $k_{expand}$ is a constant that determines the degree of expansion (this may also be denoted the expansion factor), wherein the expansion factor is a dimensionless constant. According to the present invention a value of 4 is selected for $k_{expand}$. However, in variations a value of the expansion factor in the range between 2 and 6 may be selected.

Subsequently the gain is applied to the current value $x_k(n)$ of the given frequency band signal in accordance with the formula:

$$z_k(n)=x_k(n)G_k(n)$$

wherein $G_k(n)$ represents the gain $G_k'(n)$ after it has been transformed back to the linear domain.

According to the present embodiment the same value for $k_{expand}$ is used for all the frequency bands considered.

However, in variations the gain calculated in one frequency band may be applied in another band. The inventor has found that this variation may be used to provide an enriched sound that some people find particularly attractive.

According to another variation a determined level difference in a first frequency band signal is used to calculate the gain to be applied to a second frequency band signal different from the first frequency band signal.

According to the present embodiment the reference level is selected such that the processed current value $z_k(n)$ is kept within the available dynamic range of the hearing aid system. The shape of the signals provided by the signal expander 107 (i.e. the processed current value $z_k(n)$) does not depend on the selected reference level.

However, according to a specific variation the reference level may be calculated dynamically, e.g. based on the signal from the acoustic-electrical input transducer 101. According to another variation the reference level is made dependent on the frequency band, whereby e.g. a bias of the generated noise signal may be compensated.

The processed frequency band signals (that in the following may also be denoted the expanded frequency band signals) are subsequently provided to the gain equalizer 110. The gain equalizer 110 applies a frequency dependent gain to each of the expanded frequency band signals in order to compensate the frequency dependent hearing loss of the individual hearing aid system user. This is advantageous in case the enriched sound is to be provided at a certain level above the hearing threshold. Especially it may be advantageous in case the enriched sound is used for alleviating tinnitus, since this often requires the level of the enriched sound to be in the range of 0-20 dB above the hearing threshold (i.e. in the range of 0-20 dB SL).

In a variation according to the present embodiment the effect provided by the gain equalizer 110 may be obtained by using frequency dependent reference levels that are selected based on at least one of the following: the hearing threshold of the individual hearing aid system user and the desired sensation level of the enriched sound.

In a next step the expanded and gain equalized frequency band signals are led to the inverse filter bank 108 wherein the signals are combined to a processed broadband signal, (which in the following may also be denoted the output signal). Thus according to the present embodiment the inverse filter bank 108 is simply a combination unit that adds the frequency band signals together.

However, according to another variation, the filter bank 105 transforms the white noise signal into the time-frequency domain, wherein the signal expansion may be carried out in a manner analogue to the method disclosed in the embodiment of FIG. 1, and in that case the inverse filter bank 108 is configured to carry out the transformation from the time-frequency domain and back to the time domain.

The processed broadband signal is subsequently presented to the output transducer 103 of the hearing aid using the summing node 109, which is positioned in the main signal path of the hearing aid system 100 downstream of the main digital signal processor 102. The resulting enriched sound resembles quite closely the natural sound of water running in a small stream.

The advantage of providing the processed broadband signal directly to the output transducer 103, and hereby bypassing the main digital signal processor 102 of the hearing aid, is that the enriched sound will be provided to the hearing aid system user at a stable loudness level since the enriched sound is independent on the sound environment.

Figure 2:
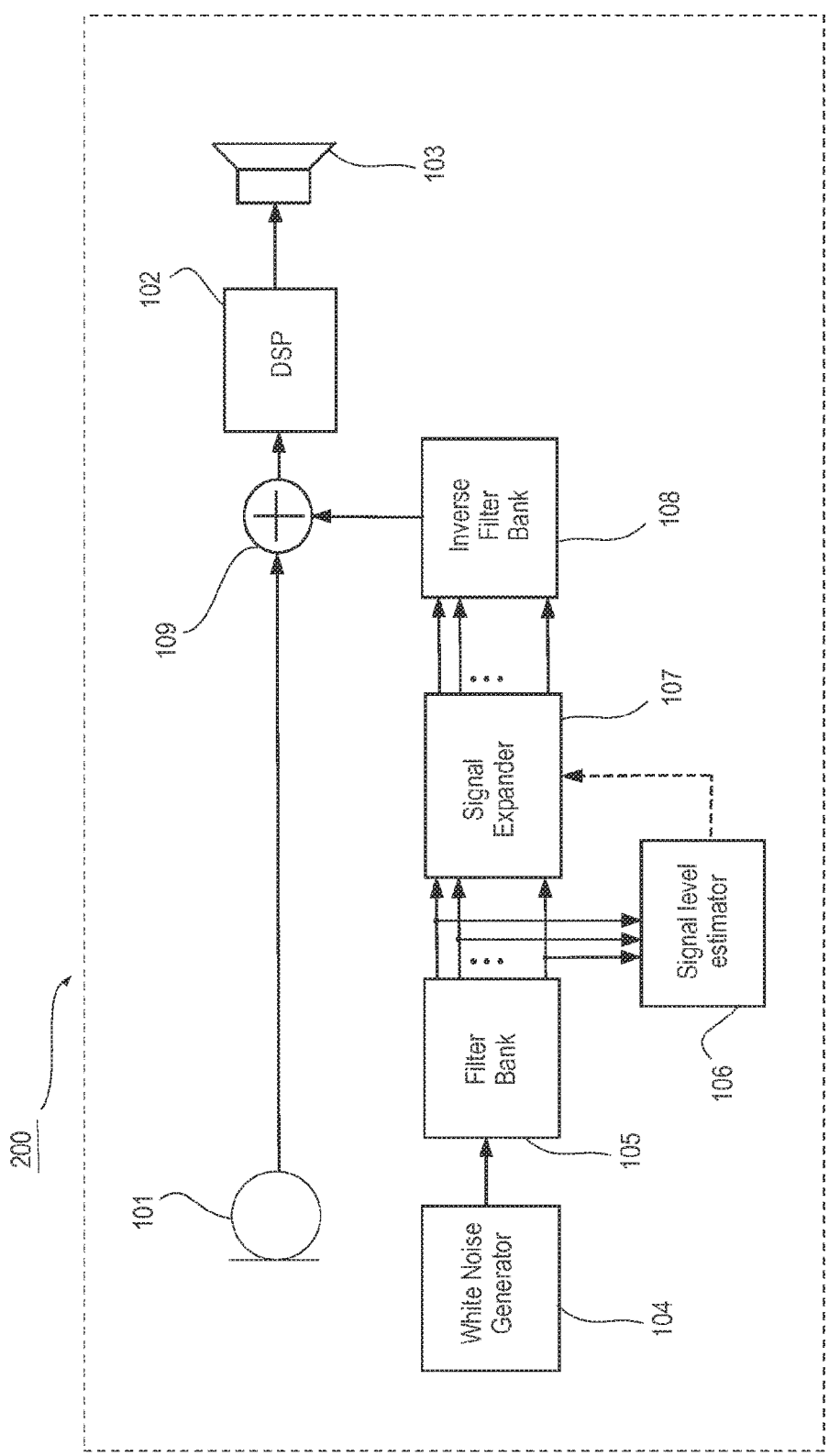
FIG. 2 illustrates highly schematically a hearing aid system according to a second embodiment of the invention.

Reference is now given to FIG. 2, which illustrates highly schematically a hearing aid system 200 according to an embodiment of the invention.

The hearing aid system 200 is similar to the hearing aid system 100 of FIG. 1 except in that the processed broadband signal is fed into the main signal path of the hearing aid system 200 upstream of the main digital signal processor 102.

It is noted that a hearing aid compressor is an essential part of most contemporary hearing aid digital signal processors and that the time constants associated with most contemporary hearing aid compressors are much slower than the time constants provided by the signal level estimator 106, and consequently it is no problem for the processed broadband signal to be added to the main signal path of the hearing aid system 200 upstream of the main digital signal processor 102.

According to a variation of the disclosed embodiments the phase of the processed frequency band signals may be adjusted. According to a specific variation of the disclosed embodiments the inventor has found that phase reversal of every other processed frequency band signal provides an enriched sound that is particularly attractive to listen to. As will be well known for a person skilled in the art this may easily be obtained by applying a linear gain of −1 to every second processed frequency band signal.

The inventor has found that this has a surprisingly strong impact on the enriched sound provided. It may be that this is a consequence of the additional modulation of the frequency spectrum that results from combining overlapping frequency band signals of opposing phases.

In a further variation the phase reversal is applied to every other frequency band signal instead of applying the phase reversals to the processed frequency band signals.

According to a specific variation of the disclosed embodiments the volume of the processed frequency band signals are attenuated to a level where only a few signal peaks are above the hearing threshold. According to a further more specific variation the attenuation is combined with a higher expansion in the higher frequency bands, such as the frequency bands above 5 kHz.

The inventor has found that such settings can provide an enriched sound that resembles the crackling sound of a campfire or the background noise of a traditional analog gramophone player.

According to another variation the inverse filter bank 108 may be omitted and the processed frequency band signals added at a point in the main hearing aid signal path where the signal is split into corresponding frequency bands.

According to still another variation the processed broadband signal is randomly modulated with a time constant significantly slower than the time constant of the signal level estimator 106. This provides an enriched sound that is particularly comfortable and relaxing to listen to for some people.

According to yet another variation the inventor has found that these types of enriched sounds may advantageously be combined with other sounds that are not necessarily as broad band as the various types of expanded white noise disclosed here. Especially the inventor has discovered that some hearing aid system users find it particularly attractive to listen to such a combined sound, wherein these other sounds at least resemble those of musical instruments. Particularly, it may be advantageous to combine the sounds according to the present invention with sounds provided using the methods disclosed in the U.S. Pat. No. 6,816,599 B2.

According to still other variations the disclosed methods of operating a hearing aid system may also be used in sound enrichment devices, designed e.g. for relieving tinnitus and characterized in that these devices have no means for compensating a hearing loss.

According to another variation of the disclosed embodiments the hearing aid system comprises a first and a second hearing aid, which are adapted to exchange information using a wireless link. The exchange of information is used to synchronize at least one aspect of the enriched sound provided by said first and second hearing aids and said aspect is selected from a group at least comprising: a time constant of the signal level estimation and the random modulation of the processed broadband signal.

According to still another variation of the disclosed embodiments the value of an expansion factor is randomly modulated and according to a more specific variation the value is modulated within a range spanning from half the value of the expansion factor and to two times the value of the expansion factor.

The invention claimed is:

1. A method of operating a hearing aid system comprising the steps of:
    generating a first electrical signal representing noise;
    filtering said first electrical signal in a filter bank hereby providing a plurality of frequency band signals,
    determining a reference level for a frequency band signal;
    estimating a signal level for said frequency band signal;
    calculating a level difference between the estimated signal level and the reference level for said frequency band signal;
    determining a gain value to be applied to said frequency band signal based on said level difference and an expansion factor;
    applying said gain value to said frequency band signal hereby providing a processed frequency band signal;
    providing a plurality of processed frequency band signals;
    summing said plurality of processed frequency band signals into an output signal; and
    presenting said output signal to the output transducer of a hearing aid.

2. The method according to claim 1, wherein the step of estimating the signal level for said frequency band signal is characterized in that the time constant of the signal level estimation decreases with the center frequency of the respective frequency band signals.

3. The method according to claim 1, wherein the current signal level estimate $y_k(n)$ for a given frequency band k and for a sample n is determined in accordance with:

$$y_k(n)=|x_k(n)|\times\alpha_k+y_k(n-1)\times(1-\alpha_k)$$

wherein $y_k(n-1)$ is the previous signal level estimate of the given frequency band signal, $x_k(n)$ is the current value of the given frequency band signal and $\alpha_k$ is a constant that determines the time constant of the signal level estimation.

4. The method according to claim 3, wherein the current value of a given frequency band signal $x_k(n)$ is sampled with a frequency in the range between 16 and 64 kHz.

5. The method according to claim 3, wherein the values of the constants $\alpha_k$ for the given frequency bands are selected to be in the range between 0.0 and 0.1 and wherein the values are further selected to increase with increasing center frequency of the respective frequency bands.

6. The method according to claim 1, wherein the gain value to be applied to a given frequency band signal is determined as the level difference multiplied with the expansion factor.

7. The method according to claim 1, wherein the expansion factor is selected to be in the range between 2 and 6.

8. The method according to claim 1, wherein the first electrical signal represents white noise.

9. The method according to claim 1, wherein the values of the expansion factor for the frequency bands are selected to increase with increasing center frequency of the respective frequency bands.

10. The method according to claim 1, wherein the reference level is determined as an average level of the first electrical signal.

11. The method according to claim 1, wherein a gain value determined for a first frequency band signal is applied to a second frequency band signal different from the first frequency band signal.

12. The method according to claim 1, wherein a determined level difference in a first frequency band signal is used to calculate the gain to be applied to a second frequency band signal different from the first frequency band signal.

13. The method according to claim 1, wherein the step of filtering said first electrical signal in the filter bank provides at least 5 frequency band signals.

14. The method according to claim 1, wherein the step of filtering said first electrical signal in the filter bank provides a plurality of frequency bands that spans the frequency range from 0-15 kHz.

15. The method according to claim 1, comprising the step of:
    adjusting the phase of a plurality of frequency band signals such that a plurality of neighboring frequency band signals have opposing phases.

16. The method according to claim 1, comprising the step of: randomly modulating the output signal with a time constant that is slower than the time constant of the signal level estimation.

17. The method according to claim 1, comprising the step of: synchronizing at least one aspect of the enriched sounds provided by a first and a second hearing aid of the hearing aid system.

18. A hearing aid system comprising:
    a random noise generator adapted to provide a random noise signal;
    a filter bank configured to provide a plurality of frequency band signals from the random noise signal;
    a signal level estimator adapted to provide a frequency band signal level estimate for the plurality of frequency band signals;
    a signal expander adapted to expand the dynamic range of the plurality of frequency band signals, hereby providing a plurality of expanded frequency band signals;
    an inverse filter bank adapted to sum the expanded frequency band signals hereby providing an output signal; and
    an electrical-acoustical output transducer for converting the output signal into enriched sound.

19. The hearing aid system according to claim 18, wherein the random noise generator is a white noise generator.

20. The hearing aid system according to claim 18, comprising a gain equalizer adapted to apply a frequency dependent gain to a plurality of the expanded frequency band signals in order to compensate the frequency dependent hearing loss of the individual hearing aid system user.

21. The hearing aid system according to claim 18, comprising a phase manipulator adapted to adjust the phase of a plurality of frequency band signals such that a plurality of neighboring frequency hand signals have opposing phases.

22. The hearing aid system according to claim 18, comprising a summing node, which is positioned in the main signal path of the hearing aid system and adapted to provide the output signal to the electrical-acoustical output transducer.

23. The hearing aid system according to claim 18, comprising:
    a wireless link between a first and a second hearing aid of the hearing aid system, a synchronization unit adapted to synchronize at least one aspect of the enriched sound provided by said first and second hearing aids respectively.

\* \* \* \* \*